(12) United States Patent
Neev et al.

(10) Patent No.: US 6,717,102 B2
(45) Date of Patent: Apr. 6, 2004

(54) LASER TISSUE PROCESSING FOR COSMETIC AND BIO-MEDICAL APPLICATIONS

(76) Inventors: Joseph Neev, 20321 Lake Forest Dr., Suite D-6, Lake Forest, CA (US) 92630; Yoram Fisher, 345 Colebourne Rd., Rochester, NY (US) 14609

( * ) Notice: Subject to any disclaimer, the term of this patent is extended or adjusted under 35 U.S.C. 154(b) by 0 days.

(21) Appl. No.: 09/878,003

(22) Filed: Jun. 8, 2001

(65) Prior Publication Data

US 2002/0088779 A1 Jul. 11, 2002

Related U.S. Application Data

(60) Provisional application No. 60/210,532, filed on Jun. 8, 2000, provisional application No. 60/214,530, filed on Jun. 27, 2000, provisional application No. 60/215,657, filed on Jul. 1, 2000, and provisional application No. 60/272,653, filed on Feb. 28, 2001.

(51) Int. Cl.[7] .............................................. B23K 26/36
(52) U.S. Cl. ............................ 219/121.68; 219/121.69; 427/554
(58) Field of Search ...................... 219/121.68, 121.69; 427/554, 555, 556

(56) References Cited

U.S. PATENT DOCUMENTS

| | | | | |
|---|---|---|---|---|
| 4,997,994 A | * | 3/1991 | Andrews et al. | 219/121.68 |
| 5,741,559 A | * | 4/1998 | Dulaney | 427/554 |
| 5,760,367 A | * | 6/1998 | Rosenwasser et al. | 219/121.69 |
| 5,824,374 A | * | 10/1998 | Bradley, Jr. et al. | 427/555 |
| 5,828,491 A | * | 10/1998 | Neuman et al. | 219/121.68 |
| 6,370,304 B1 | * | 4/2002 | Mills et al. | |
| 6,451,421 B1 | * | 9/2002 | Robertson et al. | 427/554 |

FOREIGN PATENT DOCUMENTS

| | | | |
|---|---|---|---|
| JP | 5-329667 A | * | 12/1993 |
| JP | 9-115364 A | * | 5/1997 |

* cited by examiner

*Primary Examiner*—Geoffrey S. Evans

(57) ABSTRACT

A method and a device for modifying target material for esthetic or biomedical applications. A source of energy is directed to apply the energy to a region of the tissue, so as to ablate or modify a portion of the tissue in the region allowing the creation of a desired esthetic pattern or target perforation for product, drug or nutrient delivery. Preferably, cooling of tissue in the region is initiated subsequent to the ablation.

4 Claims, 5 Drawing Sheets

LASER TISSUE PROCESSING FOR COSMETIC AND BIO-MEDICAL APPLICATIONS

CROSS-REFERENCE TO RELATED APPLICATION

This application claims priority from U.S. provisional patent application No. 60/210,532, entitled, LASER ENGRAVING FOR COSMETIC AND BIO-MEDICAL APPLICATION, filed Jun. 8, 2000, U.S. provisional application No. 60/214,530, filed Jun. 27, 2000, U.S. Provisional Application No. 60,215,657 filed Jul. 1, 2000, and U.S. Provisional Application No. 60/272,653, entitled METHOD AND DEVICE FOR MATERIAL CONDITIONING filed Feb. 28, 2001, all of which are assigned to the assignee of the present patent application and all of which are incorporated herein by reference.

FIELD OF THE INVENTION

The present invention relates generally to the application of energy to materials and biological tissue, and specifically to the application of electromagnetic energy to soft and hard tissue in order to create a desired predetermined esthetic pattern or a perforation pattern to allow a substance to penetrate surface layer barrier.

BACKGROUND OF THE INVENTION

Applications of optical sources for drilling various material including biological soft and hard tissue has been investigated over the past thirty years. Such applications included the use of lasers to remove material, cut tissue or precisely machine wafers in electronic applications.

The simplest way to generate a predictable drilled hole pattern in a material is to use an amplitude mask consisting of the required spatial configuration. Such a mask allow variations in the amplitude of the impinging energy source to be transmitted. For this reason such a mask is called an amplitude mask. It can be used in the optical case, in a near-field configuration and then a scaled up version of the desired focal pattern are made to create the pattern in a larger scale. Such a scheme, however, suffers from the drawback that most of the energy is not utilized but is wasted on absorption in the mask, where such energy is wasted as heat and does not serve a useful purpose of creating the patterns.

An alternative method employs means for focusing and stirring the beam to the desired spot. This method has the advantage of conserving laser energy but the disadvantage of sequential drilling which means longer processing time.

Another way of avoiding the waste of energy associated with amplitude masks is employing means for spatially re-distributing the energy so that the beam energy is split up into several beams and interacts simultaneously with multiple locations on the target. One such method of re-distributing the energy in space is, in the case of electromagnetic energy, employing a phase plate. A phase plate is constructed with various optical thickness (OT) over its cross-section and is placed in the path of the laser beam. The electromagnetic beam having transverse through different sections of the phase plate undergoes different phase delays. It is possible to design the phase plate (or other means for changing the wave front energy distribution of the wave front) in such a way that the original beam energy is focused on the target to form any desirable distribution pattern.

The technology of optical phase plate can be very useful to several areas of medicine. In general, the ability to divide a single beam output into several beamlets can revolutionize many applications of lasers in medicine and biology, save time, cost and in many cases, improve or provide for the execution of procedures that hitherto were not possible using a single beam techniques.

Some of the envisioned applications are:

Transdermal delivery: The stratum corneum in the human skin provides the principal barrier that limits the percutaneous penetration of topical drugs to blood vessels. This barrier can be penetrated in a very precise and minimally destructive way through the application of ultrashort pulse lasers. As we have shown previously, lasers are highly efficient in converting optical energy to remove biomedical tissue. In a similar manner, the human nail plates (of either fingers or toes) or the skin stratum corneum can be precisely ablated to form a predetermined perforation pattern which is ideal for accessing the visualized nail bed, thus allowing the coupling of drugs to the body circulatory system. The hole pattern can be generated through any number of laser sources. However, as we have shown in previous studies, because the USPL is capable of extreme precision and minimal collateral damage, we anticipate that it will even be possible to generate hole pattern of sufficiently large total surface removal yet individual holes small enough so that external organic as well as inorganic contaminant penetration is significantly minimized.

Currently, there are no other competing methods to generate controlled skin penetration other than tape-stripping which is both painful and exposes very large surfaces of the skin.

A second class of applications, is the generation of perforation pattern to circumvent and treat a common yet persisting problems in the fields of preventive and restorative dentistry. Here enhanced bond strength is conventionally obtained through phosphoric acid etching. A hole pattern ranging from $10\,\mu m$ to $100\,\mu m$ in diameter (0.1 to 2 mm deep, although optimal depth will be determined experimentally and will vary with age and tooth conditions) that would serve to enhance bond strength in a reliable predictable and reproducible manner and will be significantly superior to conventional methods. Such enhanced bonding will be used in laminated vaneers coating of tooth anterior where significant leakage and caries formation occurs in the juvenile population. Drilling an "anchor" pattern for massive amalgam fillings where currently a single screw is used to secure the large mass to the drilled hole bottom. Since current cavity preparation techniques also require a wedge shape cavity for enhancing filling retention, considerable amount of healthy tissue must be removed. Consequently, minimizing the amount of material removed while inducing superior bond strength are the two main objective of our proposed LDPG. Finally, enhanced retention of dental crowns and bridges can also be generated using the same LDPG techniques. Bond strength and filling retention properties are expected to increase dramatically.

Additional applications of controlled hole pattern generation are:

ENT—Middle ear bone surgery—creating a hole pattern for attachment of prostases, transfer of prostese motion for restoration of mechanical vibration-transmitting chain.

Orthopedics—Arthroscopic surgery (partial neniscectomy, synovectomy, chondroplasty); cartilage and tendon removal; bone incisions; microperforation, resurfacing and texturing of cartilage, tendon and bone, preparation of surface for restorative device implantation.

Angioplasty, Arheroscleratic plaque removal and preparation of vascular surfaces for stent insertion

TANSMYOCARDIAL LASER REVASCULARIZATION (TMRL)

Laser Treatment of Heart Diseases

TANSMYOCARDIAL LASER RE-VASCULARIZATION (TMRL) is a technique that brings blood directly to oxygen-deprived tissue from INSIDE the heart itself by drilling array of holes in the heart muscle. The phase plate approach enables drilling many holes simultaneously, with big effective f# giving a possibility to drill cm long channels without any additional equipment (fiberoptics etc).

In general, this technique can be used for crater pattern generation, micro perforation, precise ablation, sculpting, resurfacing, and texturing of all inorganic and organic materials and biological tissue (soft and hard).

Arterial blockages are a common cause of coronary artery disease, the No. one killer worldwide. According to the American Heart Association more than 1.5 million Americans suffer heart attacks each year. One-third die as a result.

The TMLR takes a different approach—instead of bypassing or widening a clogged artery, blood is brought directly to oxygen-deprived tissue from INSIDE the heart itself!

Current experimental procedures use Carbon-dioxide laser to vaporize tiny holes through the heart's outer walls, creating channels that bring blood directly to oxygen-starved tissue. Others have utilized TMLR using a Holmium:YAG or excimer lasers. Yet others have tested fiberoptics-based Intraoperative Tansmyocardial Revascularization (ITMR) for both surgical and catheter-based percutaneous (minimally invasive) TMLR methods.

TMLR has several advantages: operating time is ONLY 1–2 hours Operation is performed on a BEATING heart (by synchronizing the laser firing with electronic signal from the heart—EKG machine.) The laser drill 20 to 30 1 mm diameter holes through the muscular wall of the left ventricle.

Blood fills the channels, bringing in oxygen to the starved tissue. The exterior wall of the heart heals quickly.

A key to the success of the operation is knowing where to aim the laser. This is accomplish by injecting the patient with a radioactive chemical that is readily taken by the health heart cells. On an imaging scan blood deficient stand out in sharp contrast to healthy tissue. With the oxygen-deprived tissue identified, the surgeon makes a 4-inch incision between the ribs, exposing the left ventricle. A computer synchronized with the patient heartbeats waits for the less than 1/20 second interval between each beat. This interval is used to fire the laser. Examination of hearts of patients who underwent the procedure showed that the interior surfaces of the laser-bored channels shows that they grow a layer of the same type of cells that line natural blood vessels. Blood vessels were also shown to develop from the SIDES of the laser-drilled channels.

Already (with trial laser procedures) hospital stay after the laser surgery may average six days or even less, as opposed to 11 days for a bypass operation. It is also expected that laser operation and smaller holes will reduce healing time. Drilling multiple channels will limit thermal damage, more closely mimic natural vascularization and may allow us to control the rate of channel closure. Using phase plates for simultaneous whole drilling or rapid beam manipulations in combination with light-based systems further limit and control thermal damage and would further shorten healing times.

Finally, the laser-drilled channels have formed walls similar to those found in healthier blood vessels. (i.e. the channel actually become—new blood vessels!) Clearly, the rapid rate of drilling using multiple beamlets will drastically reduce both procedure and healing time.

SUMMARY OF THE INVENTION

An energy source is focused down to power densities sufficient for ablating a fingernail without producing painful heat or damage to the underlying layers. By controlling the spot size, energy, and pulse duration a pattern may be formed in the target. The depth and shape of the pattern can be varied from a very light surface modification to penetration through the entire nail. Two computer-controlled scanners steer the laser beam to form an arbitrary pattern. Modulation of the laser beam can be accomplished electronically or mechanically. The pattern of drilled holes thus formed may be utilize to perforate of a barrier layer to allow delivery of a substance across a the barrier layer.

DETAILED DESCRIPTION OF PREFERRED EMBODIMENTS

Figure 1:
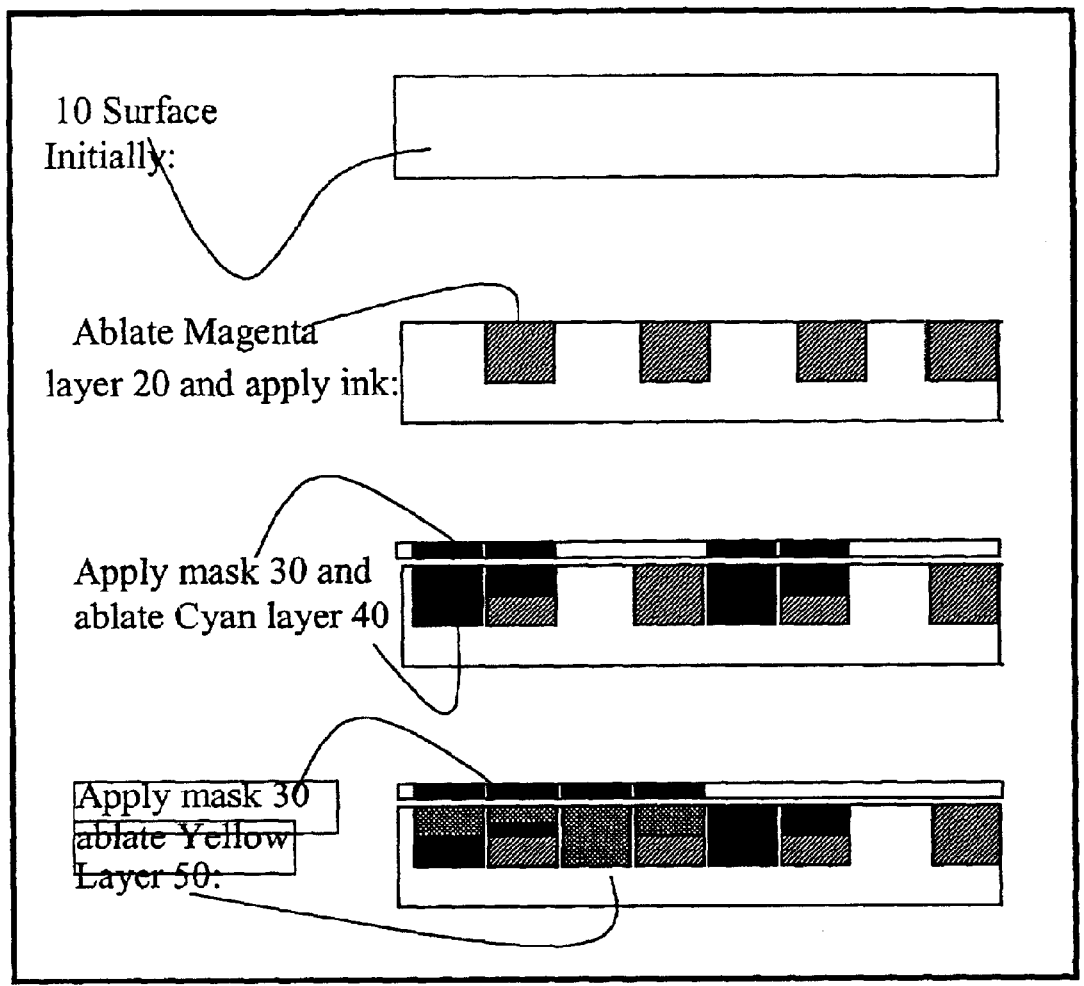
FIG. 1 is a simplified graphic illustration of a cross section of a hard tissue surface showing individual pixels filled with a combination of colors.

A preferred embodiment for the creation of full color tattoos is shown in FIG. 1. The color image is broken into its 3 RGB components. The subtractive colors (Cyan, Yellow, and Magenta) are derived from the image. The target material 10 is first etched with the Magenta component of the image 20. Each color is dithered using a standard dithering algorithm such as Floyd-Steinberg or Stucki. The Magenta ink is applied and wiped, leaving ink only in the etched portions of the nail. Then a mask 30 is applied to the nail, and the target is placed back to its original position. One simple method for doing this is to place the target in a soft clay mold initially so that the finger registers back to the same position each time.

The mask can be made of a thin adhesive layer that block the ink, but does not affect the laser beam. For example Scotch tape works well. Next, the Cyan layer 40 is etched into the target 10. The device software adjusts the Cyan pixels that overlap with Magenta pixels. The laser power on overlapping pixels is adjusted so that the mask is punctured, but the existing hole in the nail is not increased in depth. Thus, pixels that contain Magenta and Cyan will not be twice as deep. Rather, the Cyan will slightly cover the Magenta. Some of the Magenta ink will ablate out leaving room for the Cyan. The Cyan, being a lighter color than Magenta, will allow for optical mixing of both colors on that pixel. The Cyan is applied and then the mask is removed.

This process is repeated for the Yellow layer 50, where yellow is the lightest color. This order of colors gives the best color mixing. For Yellow pixels, the power is reduced for locations that already contain Magenta or Cyan. Upon removal of the last mask 30, there is a full color image. The color image is substantially permanent, but can be clear coated with regular clear nail-polish for better durability and shine.

An alternative and simpler method for the creation of full color tattoos is to avoid having multiple colors on the same pixel altogether. Pixels that share two or more colors would randomly be assigned one of the original colors. Thus the dithering of colors would produce both intensity variations and color variations. All pixels would be the same depth and have one color only. The process of three colors, and two masks would otherwise be identical as described above.

A Preferred Embodiment for Tattoo Design

A full sized tattoo that covers most of the fingernail will eventually grow out to the point where the nail must be clipped. This will leave only a portion of the tattoo remaining. For customers who do not want to let their nails grow long enough that the tattoo can be clipped off in its entirety, there is another solution illustrated in FIG. 2. The imprinted image 120 can be made small, along the outer edge of the nail 100. The tattoo image 120 is smaller and less visible, and will last approximately 2–3 weeks. It can then be clipped entirely and the nail is ready for a new tattoo. Alternatively, the nail may be allowed to grow and esthetically trimmed to the desired shape and configuration. This will allow the tattoo on the nail to last a long time. A third embodiment envisions a dynamic tattoo where the tattoo move along with the growing nail, and additional images are added to the new sections of the nail.

Figure 3:
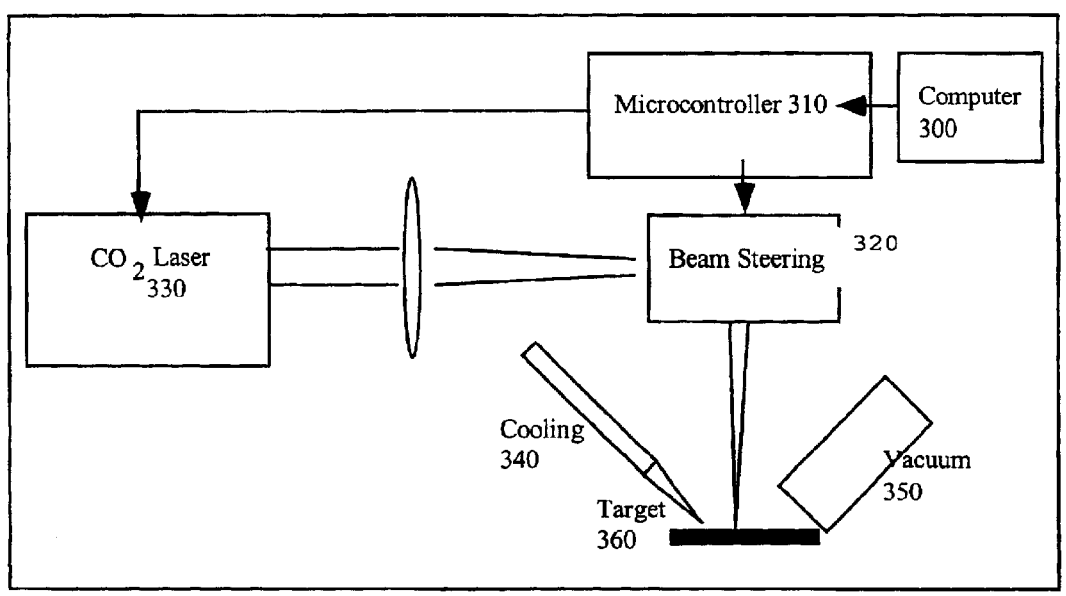

FIG. 3 shows a representative exemplary preferred embodiment for a device for tissue engraving. Typical parameters for a CO2 laser with 10–30 Watts power, a 100 $\mu$m spot size, and a 1 cm by 1 cm coverage. The total time to write one color is 10–60 seconds, depending on the size and resolution chosen. The microcontroller 310 is connected to a computer 300 via RS232 or similar. The computer holds the raw bitmap images, and the software to process color images and convert them to binary data used by the microcontroller. The microcontroller 310 controls the laser 330 and the laser beam steering 320 via two A/D outputs that control the x and y galvanometers. It also modulates the laser output via an electronic gate. The cool air or other cooling or energy removal source 340 removes heat rapidly after the interaction is completed at the target surface 360, and the vacuum 350 line removes smoke and unpleasant odors The process is fairly quick, completely painless, and produces very sharp and colorful permanent designs. The image is easily read in by computer and could be a photograph that the customer brings in or even a doodle that they can draw themselves with any graphics program on any computer.

Any word or phrase can be etched into the fingernail. The etching is typically 100–200 $\mu$m deep and is permanent, until the nail has grown and the tattoo has been cut away (1–3 months depending on the size of the tattoo). Colorful ink can be pressed into the resultant etching, leaving a very clear design, which is permanent. The thin, deep etching holds the ink well. The ink does not wash out with soap and water. Any leftover ink or undesired spots at the surface can be removed or polished off to leave only the ink in the depression.

Bitmap images can also be used to produce text of any font, logos, and images. Using a slightly more elaborate process, full-color nail tattoos can be made.

Other material can be etched as well: Customers can bring in most any materials. Plastics and glass etch well with approximately 20 Watts. For metals, semiprecious jewelry, or ceramics a higher power laser could be used (60–200 Watts).

Figure 4A:
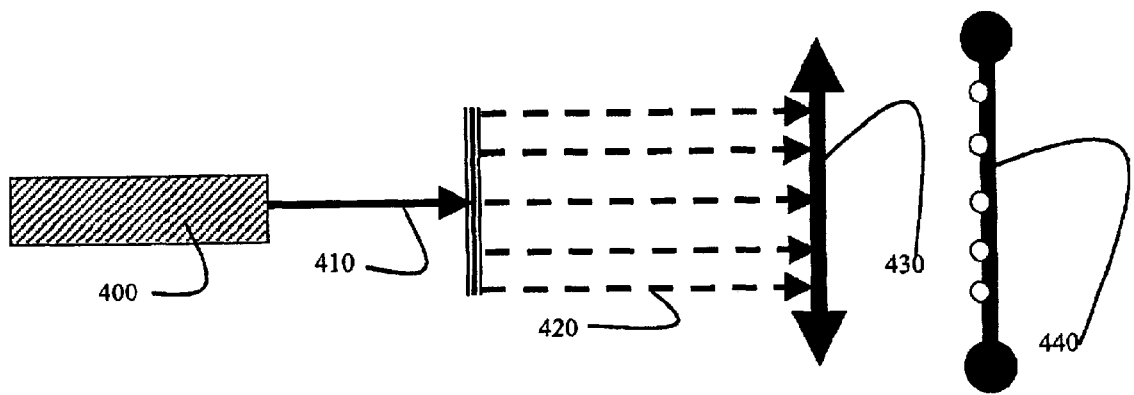
FIGS. 4a and 4b are an simplified graphic illustrations showing the redistribution of single beam energy to multiple beamlets to allow multiple craters formation using a single source beam.
Figure 4B:
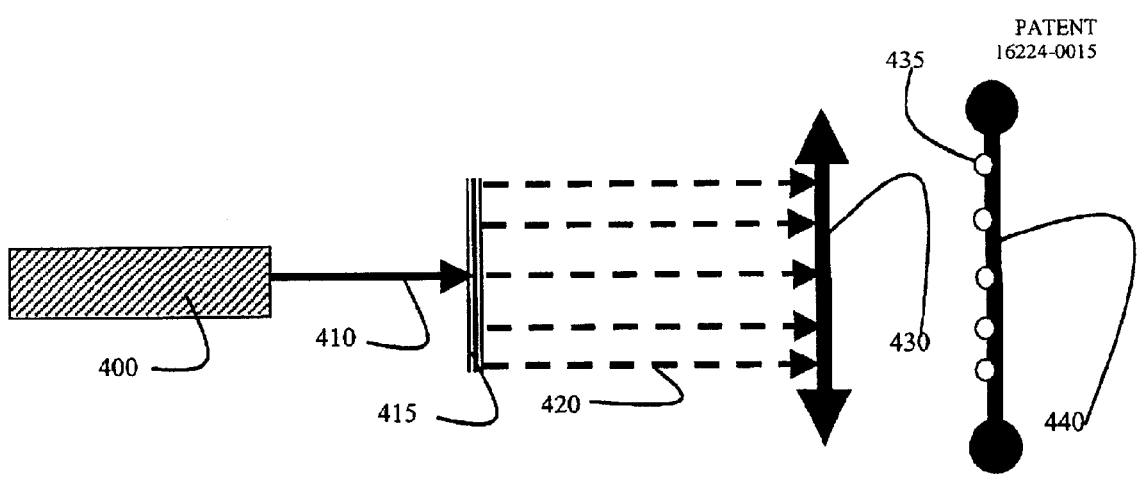

FIG. 4 shows another preferred embodiment utilizing a single source, 400, which is then split by redistributing the single beam 410 energy using such optical components such as optical phase plates 415, to split the single beam 410 energy to multiple beams 415.

The beams are then focused by the lens 430 to create a crater or hole pattern 435 on a target surface 440.

Trans-tissue Drag and Product Delivery

Figure 2:
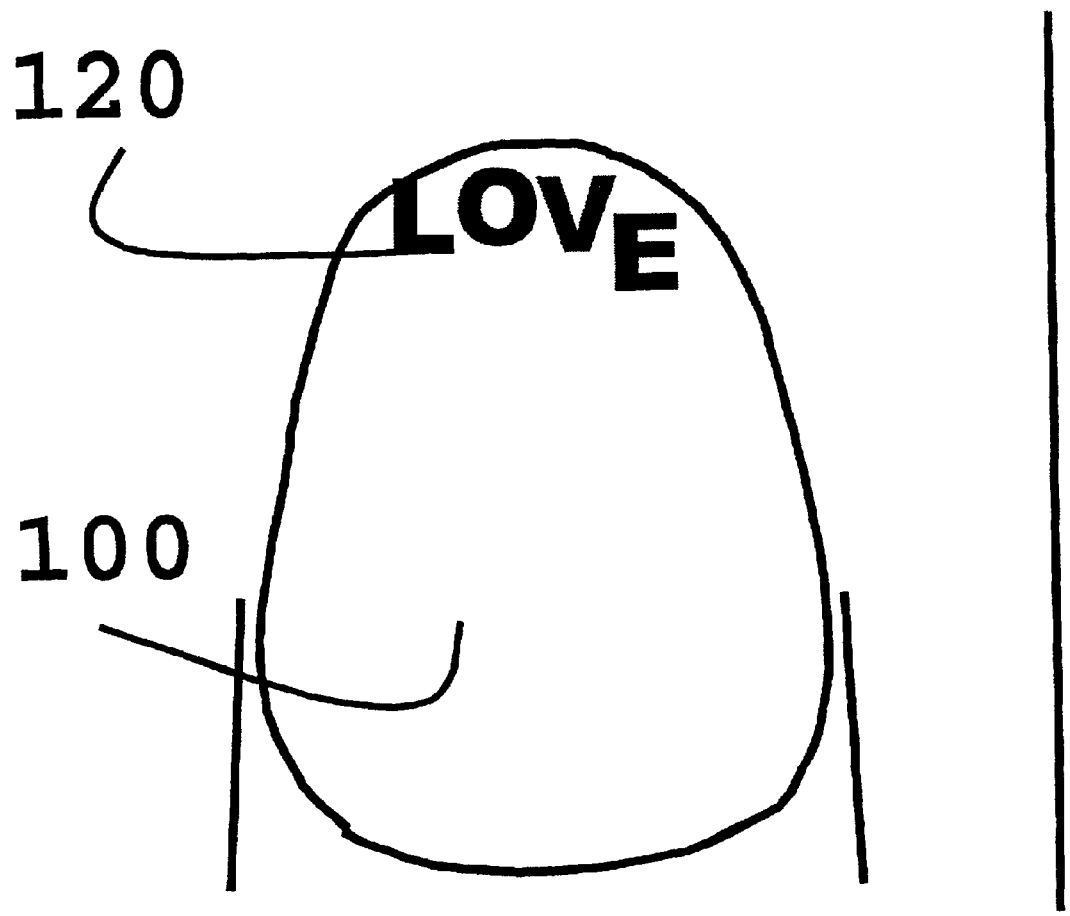
FIG. 2. is a simplified graphic illustration of a imprinted color pattern on the an exemplary hard tissue of a human nail FIG. 3. is a simplified graphic illustration of a device for a target material engraving.

The patterns generated by the methods described in FIG. 1 and FIG. 4, and illustrated by the exemplary illustration of FIG. 2, can be used for continuous drug, products or nutrient delivery to the skin and blood vessels within the body. For example, the delivery of insulin to diabetic patient is envisioned as one exemplary application. In this application, a perforation pattern is established in the skin or the nail, and the drug is applied to the surface to allow drug or product delivery. The application of drug can be accomplished be attaching a drug reservoir to the skin or nail. For example, an artificial nail can be attached to the perforated real nail surface. In such cases, the perforation/craters in the nail or skin must be deep enough to allow the product or drug to reach the blood vessels below the epidermis or below the nail. One such application may be utilizing a simple home device for such a use.

One preferred embodiment of drug/product delivery envision the following device comprising:

An energy source, (preferably a diode laser of relatively lower power and wavelength that is transmitted well in tissue and is NOT well absorbed by the skin or nail of human (or animals)). Optical components and scanners to move the beam over a typically area (typically such area shall be smaller than 4 $cm^2$);

A substance capable of absorbing much of the source's energy beam,

A dispenser capable of dispensing said high absorbing substance into specific desired locations (for example, placing the high absorbing substance directly over a previously drilled craters), And an optional energy removing substance, capable of being applied to the target surface of skin or nail after the interaction is completed and removing excess heat from the target surface to eliminated or minimize discomfort.

Such a device can be low power, safe (self contained, the patient or user NEVER sees the light beam or interaction) and low cost.

The user can for example, every two days or so, apply a biological compatible, safe, and non-toxic high absorbing substance to his/her nail or skin, (preferably to locations that has already been drilled before—for example, such locations may be created initially by a health professional and then maintained open by once a day or once every few days use of the device described herein) Such a substance can be precisely applied, for example, by the patients themselves, (for example, manually, with a brush) to the location of the previously drilled spots. The amount and density of the high absorbing substance, for example, can also be adjusted (by adjusting the properties of the high absorbing substance) to determine the depth of the drilled crater.

The patient then, apply the substance to the desired locations, then apply the devise (with a preferred diode laser as energy source) over the skin or nail surface, and then apply the reservoir containing the drug, nutrient or product (desired to be delivered to the blood vessels) to the perforated target surface. The Device scan rate, focus, energy removal parameters or characteristics and parameters of the high absorbing substance can be adjust to allow a predetermined desired permeability of the surface. (In an alternative preferred embodiment, the reservoir containing material can be adjusted to allow a predetermined desired drug or product delivery rates.) The reservoir, drug and product delivery drilled holes patter then allow a controlled, time-dependant and space dependant delivery of drug or product or nutrient to the patient body and blood vessels with little maintenance and substantially no pain, substantially no discomfort and substantially no significant esthetic impact.

It will be understood by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art which would occur to persons skilled in the art upon reading the foregoing description.

What is claimed is:

1. A method of creating a perforation pattern in a material, comprising the steps of:

directing an electromagnetic source to apply energy to a targeted region of the material to remove the targeted material in the form of craters of a desired size, shape and depth to create a first crater pattern capable of holding color pigment;

coating the targeted material with a first color component of a three color RGB color combination;

wiping the targeted material to leave the first color component only in the first crater pattern;

applying a mask to the targeted material;

applying energy to the mask covered targeted material to create a second crater pattern that overlaps with the first crater pattern, the energy being reduced so the first color in the first crater pattern is only partially removed;

coating the mask covered targeted material with a second color component which is lighter than the first color component, the second color component being applied only to the craters of the second crater pattern;

removing the mask;

repeating the applying a mask, applying energy, and coating steps using a third color component which is the most transmitting color;

removing the mask after application of the third color component to show a full color image on the targeted material; and coating the full color image with a light transmitting coat to allow better durability and shine.

2. A method of creating a perforation pattern in a material, comprising the steps of:

directing an electromagnetic source to apply energy to a targeted region of the material to remove the targeted material in the form of craters of a desired size, shape and depth to create craters capable of holding color pigment and a crater pattern; and applying a substance capable of removing the energy from the surface of the targeted material periodically after energy has been applied to at least a segment of the targeted material, to allow cooling of the surface and minimization of pain.

3. A device for creating a pattern of spots of modified physical characteristics in a target material, comprising:

an electromagnetic energy source;

a combination of movable mirrors and lenses capable of manipulating a beam of energy emerging from the energy source in order to create a desired pattern at the target material by removal of some of the material from the target material; and an intermediate material capable of absorbing the energy from the energy source located at the target material in order to enhance absorption of the energy from the energy source, causing a perforation pattern in the target material, the perforation pattern being deep enough to allow delivery of a substance through the target material to a desired depth below the surface of the target material.

4. A device for creating a pattern of spots of modified physical characteristics in a target material, comprising:

an electromagnetic energy source;

a combination of movable mirrors and lenses capable of manipulating a beam of energy emerging from the energy source to remove some of the material from the target material in order to create a desired pattern in the target material; and an intermediate material capable of absorbing the energy from the energy source located on the target material in order to enhance absorption of the energy from the energy source by the target material, the material removed from the target material creating a perforation pattern in the target material, the perforation pattern being deep enough to allow delivery of a substance through the target material to a desired depth below the target material surface.

* * * * *